United States Patent
Behler et al.

(10) Patent No.: US 6,646,145 B1
(45) Date of Patent: Nov. 11, 2003

(54) PROCESSES FOR PREPARING ALKOXYLATED NONIONIC SURFACTANTS USING HYDROTALCITE CATALYSTS

(75) Inventors: Ansgar Behler, Bottrop (DE); Horst-Dieter Schares, Erkath (DE); Almud Folge, Langenfeld (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/914,834

(22) PCT Filed: Feb. 24, 2000

(86) PCT No.: PCT/EP00/01502
§ 371 (c)(1),
(2), (4) Date: Jan. 8, 2002

(87) PCT Pub. No.: WO00/51955
PCT Pub. Date: Sep. 8, 2000

(30) Foreign Application Priority Data

Mar. 3, 1999 (DE) ......................................... 199 09 272

(51) Int. Cl.$^7$ ........................ C07C 51/00; C07C 67/24; C07C 43/11; C07C 43/18; C07C 43/20
(52) U.S. Cl. ........................ 554/149; 560/240; 568/620; 568/623
(58) Field of Search ..................... 554/149; 560/240; 568/620, 623

(56) References Cited

U.S. PATENT DOCUMENTS

| | | | |
|---|---|---|---|
| 5,012,012 A | | 4/1991 | Nakamura et al. |
| 5,292,910 A | | 3/1994 | Raths et al. |
| 5,651,997 A | * | 7/1997 | Makino et al. .............. 424/682 |
| 5,817,844 A | | 10/1998 | Hama et al. |
| 6,008,392 A | | 12/1999 | Behler et al. |

FOREIGN PATENT DOCUMENTS

| | | |
|---|---|---|
| AU | 33349/89 | 10/1989 |
| DE | 38 33 076 A1 | 4/1989 |
| DE | 38 43 713 A1 | 11/1989 |
| DE | 40 10 606 A1 | 10/1991 |
| DE | 44 46 064 A1 | 6/1995 |
| DE | 196 11 999 C1 | 7/1997 |
| EP | 0 339 425 B1 | 11/1989 |
| EP | 0 523 089 B1 | 1/1993 |
| WO | WO92/12950 A | 8/1992 |
| WO | WO 92/12950 * | 8/1992 |
| WO | WO92/12951 A | 8/1992 |

OTHER PUBLICATIONS

The Merck Index, 13$^{th}$ Ed. Merck & Co., Inc. p. 7647 (2001).*
"Neutralization Process of Synthetic Hydrotalcite with Hydrochloric Acid" Yakuzaigaku, vol. 38, No. 3, pp. 166–173 (1978).*
"Studies of neutralizing properties of antacid preparations" Z. Kokot. Pharmazie vol. 44, pp. 828–830 (1989).*

* cited by examiner

*Primary Examiner*—Richard L. Raymond
*Assistant Examiner*—Zachary C. Tucker
(74) *Attorney, Agent, or Firm*—John E. Drach; Aaron E. Ettelman

(57) ABSTRACT

Processes for preparing alkoxylated nonionic surfactants are disclosed, wherein a compound having at least one active hydrogen atom, a carboxylic acid ester or mixtures thereof are reacted with an alkylene oxide in the presence of a hydrotalcite catalyst to form a reaction product mixture; and the reaction product mixture is combined with an acid in at least an equimolar amount based on the amount of the catalyst present.

45 Claims, No Drawings

PROCESSES FOR PREPARING ALKOXYLATED NONIONIC SURFACTANTS USING HYDROTALCITE CATALYSTS

This invention relates to a process for the production of alkoxylated nonionic surtactants in which compounds containing active hydrogen atoms or carboxylic acid esters are reacted with alkylene oxides in the presence of optionally modified hydrotalcite as catalyst and optionally other selected co-catalysts and the reaction products obtained are aftertreated with acids.

An important group of nonionic surfactants are products of the addition of alkylene oxides, especially ethylene oxide and/or propylene oxide, onto compounds containing active hydrogen which are normally produced by homogeneous catalysis in the presence of alkali metal hydroxides or alkali metal alcoholates. Products with a broad homolog distribution are obtained by the homogeneously catalyzed process. Products with a narrow homolog distribution can be obtained by carrying out the reaction in the presence of optionally modified hydrotalcites, for example in accordance with DE-A-38 33 076. The alkoxylation of carboxylic acid esters also takes place with better results in the presence of hydrotalcites, the alkylene oxides being inserted into the carbonyl ester bond, for example in accordance with the two patents EP-B1-0 339 425 and EP-B1-0 523 089.

However, after the actual alkoxylation using optionally modified hydrotalcite, separation of the catalyst from the reaction product presents technical difficulties because the optionally modified hydrotalcite is generally so finely particulate that it can only be filtered through special filter candles. Unfortunately, the catalyst cannot be allowed to remain in the end reaction product either because otherwise clouding and sedimentation can occur.

Accordingly, the problem addressed by the present invention was to provide a process for the production of alkoxylated nonionic surfactants which would not have any of the disadvantages of the complex filtration or clouding and sedimentation of the end reaction product.

BRIEF SUMMARY OF THE INVENTION

Surprisingly, the problem stated above has been solved by decomposing the catalyst hydrotalcite and any co-catalysts present by addition of acids after the alkoxylation rather than removing them by filtration. The invention includes the observation that the acid aftertreatment decomposes the hydrotalcite and any co-catalysts present into products which can remain in the reaction mixture without any clouding or sedimentation subsequently occurring.

Accordingly, the present invention relates to a process for the production of alkoxylated nonionic surfactants by reaction of compounds containing active hydrogen atoms or carboxylic acid esters with alkylene oxides in the presence of optionally modified hydrotalcite as catalyst and optionally co-catalysts, characterized in that at least equimolar quantities—based on hydrotalcite and optionally co-catalysts—of acids are added after the alkoxylation.

DETAILED DESCRIPTION OF THE INVENTION

The compounds containing active hydrogen atoms may be selected, for example, from the following classes of compounds:

a1) alcohols containing 6 to 22 carbon atoms (so-called fatty alcohols) such as, for example, caproic alcohol, caprylic alcohol, capric alcohol, lauryl alcohol, myristyl alcohol, cetyl alcohol, palmitoleyl alcohol, stearyl alcohol, isostearyl, alcohol, oleyl alcohol, elaidyl alcohol, petroselinyl alcohol, linolyl alcohol, linolenyl alcohol, ricinolyl alcohol, elaeostearyl alcohol, arachyl alcohol, gadoleyl alcohol, behenyl alcohol, erucyl alcohol and the technical mixtures thereof obtained, for example, in the hydrogenation of methyl ester fractions of native origin or aldehydes from Roelen's oxo synthesis. Fatty alcohols containing 12 to 18 carbon atoms, for example technical coconut or tallow fatty alcohol cuts, are preferred.

Another group of suitable fatty alcohols are the co-called Guerbet alcohols which are produced by the alkali-catalyzed condensation of 2 moles of fatty alcohol and which may contain 12 to 36 carbon atoms.

a2) Carboxylic acids containing 6 to 22 carbon atoms (so-called fatty acids) and hydroxyfatty acids such as, for example, caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, ricinoleic acid, elaeostearic acid, arachic acid, gadoleic acid, behenic acid and erucic acid and the technical mixtures thereof obtained, for example, in the pressure hydrolysis of natural fats and oils. Fatty acids containing 12 to 18 carbon atoms, for example technical coconut oil or tallow fatty acids, are preferred.

a3) Alkyl phenols, polyglycols, fatty amines, vicinal hydroxy/alkoxy-substituted alkanes obtainable, for example, by ring opening of epoxide compounds with alcohols or carboxylic acids and secondary alcohols.

Within the group of compounds containing active hydrogen atoms, the alcohols or carboxylic acids containing 6 to 22 carbon atoms are preferred.

In another embodiment of the process according to the invention, carboxylic acid esters are used as starting materials. Basically, there are again two types of carboxylic acid esters, namely:

b1) carboxylic acid lower alkyl esters corresponding to formula (I):

$$R^1CO\text{—}OR^2 \qquad (I)$$

in which $R^1CO$ is an aliphatic acyl group containing 6 to 22 carbon atoms and $R^2$ is a linear or branched alkyl group containing 1 to 4 carbon atoms. Typical examples are esters of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, ricinoleic acid, elaeostearic acid, arachic acid, gadoleic acid, behenic acid and erucic acid and technical mixtures thereof with methanol, ethanol, propanol or butanol. Methyl esters of fatty acids containing 12 to 18 carbon atoms and, more particularly, technical coconut oil or tallow fatty acid methyl esters are preferably used.

b2) carboxylic acid glycerol esters corresponding to formula (II):

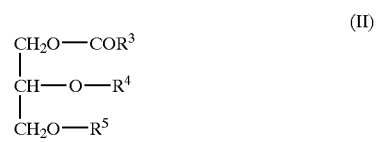

in which $R^3CO$ is an aliphatic acyl group containing 6 to 22 carbon atoms and $R^4$ and $R^5$ independently of one another represent hydrogen or likewise an aliphatic acyl group containing 6 to 22 carbon atoms.

Typical examples of such compounds are synthetic but preferably natural triglycerides, such as palm oil, palm kernel oil, coconut oil, rapeseed oil, olive oil, sunflower oil, cottonseed oil, peanut oil, linseed oil, lard oil, bovine tallow and lard. Castor oil or hydrogenated castor oil is preferably used.

In one preferred embodiment, the full esters are replaced by fatty acid partial glycerides, more particularly monoglycerides of fatty acids containing 12 to 18 carbon atoms. Technical coconut oil fatty acid monoglycerides are particularly preferred. Within the group of carboxylic acid esters, carboxylic acid lower alkyl esters, especially the methyl esters of carboxylic acids containing 6 to 22 carbon atoms, are preferred.

Optionally modified hydrotalcites are used as alkoxylation catalysts in the process according to the invention either on their own or in admixture with selected co-catalysts. In one embodiment of the present invention, optionally modified hydrotalcite is used on its own as catalyst. Calcined or hydrophobicized hydrotalcites, as known for example from German patent applications DE-A1 38 43 713 and DE-A1 40 10 606 (Henkel), are used as modified hydrotalcites. Calcined hydrotalcites are particularly preferred.

In another embodiment of the invention, optionally modified hydrotalcites and selected co-catalysts are used together as alkoxylation catalysts. Suitable co-catalysts are compounds from the group consisting of hydroxides, oxides and/or alkoxides of alkali metals and/or alkaline earth metals and of alkali metal and/or alkaline earth metal salts, tin salts and of mixed metal oxides.

Particularly suitable hydroxides of alkali metals and/or alkaline earth metals are lithium hydroxide and/or magnesium hydroxide.

Within the group of oxides of alkali metals and/or alkaline earth metals, the oxides of magnesium are preferred.

Preferred alkoxides of the alkali metals and/or alkaline earth metals are those which are derived from short-chain alcohols, for example those containing 1 to 8 carbon atoms, more particularly from methanol, ethanol and/or 2-ethyl hexanol. Magnesium and/or barium compounds are particularly preferred.

Within the group of alkali metal and/or alkaline earth metal salts, the magnesium and barium salts, for example the carbonates, such as magnesium carbonate, or the acetates, for example magnesium acetate, are particularly important.

Mixed metal oxides are oxide compounds which contain at least two different metals. One of the metals is preferably magnesium. The other metal may be aluminium, gallium, zirconium, indium, thallium, cobalt, scandium, lanthanum and/or manganese. Magnesium/aluminium mixed oxides are particularly preferred. The mixed oxides may be surface-modified with one or more of the co-catalysts already mentioned, more particularly with the hydroxides and/or alkoxides of the alkali metals and/or alkaline earth metals. Mixed metal oxides such as these and ways of modifying them are described, for example, in DE-A-44 46 064.

Magnesium oxide is a particularly preferred co-catalyst.

If the optionally modified hydrotalcites are sole catalysts, they are used in quantities of normally 0.1 to 5% by weight and preferably 0.5 to 1.5% by weight, based on starting compounds (compounds containing active hydrogen or carboxylic acid esters and alkylene oxide).

If the optionally modified hydrotalcites are used together with the selected co-catalysts, they are used in quantities of normally 0.05 to 2.5% by weight and more particularly 0.1 to 0.5% by weight, based on the starting compounds. The co-catalysts may be used in quantities of 0.05 to 5% by weight, preferably in quantities of 0.1 to 0.5% by weight and more particularly in quantities of 0.1 to 0.3% by weight, based on the starting compounds.

By virtue of the synergistic effect in catalyst activity between optionally modified hydrotalcite and the co-catalysts, it is even possible in accordance with the invention to obtain very good results with a total quantity of hydrotalcite and co-catalysts below 0.5% by weight, preferably with quantities of 0.1 to 0.4% by weight and more particularly with quantities of 0.2 to 0.3% by weight, based on the starting compounds.

The ratio between optionally modified hydrotalcite as catalyst and co-catalysts may vary within wide limits and is preferably between 5:1 to 1:5, more preferably between 3:1 and 1:3 and most particularly between 2:1 and 1:2.

The reaction of the compounds containing active hydrogen atoms or the carboxylic acid esters with the alkylene oxides may be carried out in known manner at temperatures of 120 to 200° C. and preferably 150 to 180° C. and under pressures of 1 to 5 bar. The quantity of alkylene oxide to be added on is not critical and may amount, for example, to between 1 and 100, preferably to between 2 and 50 and more particularly to between 2 and 20 moles of alkylene oxide per mole of H-active compound or carboxylic acid ester.

Ethylene, propylene and/or butylene oxide may be used as the alkylene oxide, ethylene oxide being preferred.

Now, it is crucial to the invention that, after the actual alkoxylation, the catalysts used, namely the optionally modified hydrotalcite on its own or in admixture with the selected co-catalysts, are completely decomposed in the reaction mixture obtained by the addition of acids.

Both inorganic and organic acids may be added as the acids. Suitable inorganic acids are, in particular, the mineral acids, such as sulfuric acid, hydrochloric acid and/or phosphoric acid. Suitable organic acids are both the so-called fatty acids containing 6 to 22 carbon atoms and lower carboxylic acids containing 1 to 4 carbon atoms (only the carbon atoms of the hydrocarbon chain are counted, not the carbon atoms of the carboxyl groups) which may optionally be additionally modified with hydroxyl groups. Preferred organic acids are the lower carboxylic acids, such as lactic acid, acetic acid and/or citric acid.

The acids are generally added as aqueous solutions, preferably as 10 to 90% by weight solutions.

According to the invention, the acids are used in at least equimolar quantities, based on hydrotalcite and any co-catalysts present. The actual quantity of acid added is of course dependent on the strength of the acid. Molar ratios of acid to hydrotalcite and co-catalysts, if any, of generally 1:1 to 10:1 and more particularly 1:1 to 4:1 are recommended.

In one advantageous embodiment of the invention, the acids are added at temperatures above the melting point of the alkoxylated nonionic surfactants, preferably at temperatures of 70 to 95° C. In practice, this is best done by keeping the reaction mixture obtained after the alkoxylation at those temperatures and adding the acid. The effect of adding the acid is that the hydrotalcite decomposes. The decomposition products of the hydrotalcite are soluble in water and do not lead to any clouding or sedimentation of the alkoxylated nonionic surfactants. Accordingly, there is no need in the process according to the invention for the elaborate filtration of the optionally modified hydrotalcite. If desired, the acid treatment according to the invention may of course be followed by working up of the water-soluble decomposition products of the hydrotalcite, for example by separation of the aqueous phase from the organic phase.

The present invention also relates to the use of acids for decomposing optionally modified hydrotalcite and co-catalysts present as catalyst in reaction mixtures of alkoxylated nonionic surfactants.

The alkoxylated nonionic surfactants obtained by the process according to the invention may be used without further filtration. No precipitation or sedimentation occurs, even after prolonged storage. Accordingly, they are suitable as nonionic surfactants for the production of laundry detergents, dishwashing detergents and cleaners and for the production of cleansing cosmetics, more particularly liquid products, such as liquid laundry detergents, hair shampoos and the like.

EXAMPLES

Example 1

288.6 g (=1.35 mole) of a methyl laurate were introduced into a pressure reactor together with 5.0 g (=0.5% by weight, based on starting compounds) of calcined hydrotalcite. The reactor was evacuated for 30 minutes at 100° C. and then purged with nitrogen. 711.4 g (=12 moles) of ethylene oxide were added in portions at max. 180° C. and max. 5 bar pressure. The reaction time was 150 minutes. After the alkoxylation, the reaction mixture was after-reacted for 1 hour at 120° C. and the reactor was evacuated for another 30 minutes at 120° C.

100 g of a 10% by weight citric acid were added to this reaction mixture with stirring at 90° C.

The calcined hydrotalcite had dissolved after stirring for 10 minutes. The reaction mixture obtained was clear in the melt.

Example 2

A mixture of 65.3 g (=0.41 mole) of a caprylic acid methyl ester and 261.3 g (=1.12 mole) of a methyl ester of palm kernel oil (fatty acid chain containing 12 to 18 carbon atoms) was introduced into a pressure reactor together with 1.0 g (=0.1% by weight, based on starting compounds) of calcined hydrotalcite and 2.0 g of magnesium oxide (=0.2% by weight, based on starting compounds). The reactor was evacuated for 30 minutes at 100° C. and then purged with nitrogen. 673.4 g (=10 moles) of ethylene oxide were added in portions at max. 180° C. and max. 5 bar pressure. The reaction time was 160 minutes. After the alkoxylation, the reaction mixture was after-reacted for 1 hour at 120° C. and the reactor was evacuated for another 30 minutes at 120° C.

68.4 g of a 20% by weight acetic acid were added to this reaction mixture with stirring at 90° C. The catalyst mixture of hydrotalcite and magnesium oxide dissolved completely in three minutes.

Example 3

638.3 g (=3,3 moles) of a $C_{12/14}$ fatty alcohol mixture (ca. 70% by weight $C_{12}$ alcohol and ca. 30% by weight $C_{14}$ alcohol) were introduced into a pressure reactor together with 1.0 g (=0.1% by weight, based on starting compounds) of calcined hydrotalcite and 2.0 g of magnesium oxide (=0.2% by weight, based on starting compounds). The reactor was evacuated for 30 minutes at 100° C. and then purged with nitrogen. 361.7 g (=8.2 moles) of ethylene oxide were added in portions at max. 180° C. and max. 5 bar pressure. The reaction time was 70 minutes. After the alkoxylation, the reaction mixture was after-reacted for 1 hour at 120° C. and the reactor was evacuated for another 30 minutes at 120° C.

An ethoxylated $C_{12/14}$ fatty alcohol with a hydroxyl value of 179 was obtained.

11.4 g of a 20% by weight acetic acid was added to the reaction mixture obtained with stirring at 90° C. The hydrotalcite and the magnesium oxide had dissolved completely after 15 minutes.

What is claimed is:

1. A process for preparing an alkoxylated nonionic surfactant, said process comprising:
   (a) reacting a starting material selected from the group consisting of compounds having at least one active hydrogen atom, carboxylic acid esters and mixtures thereof with an alkylene oxide in the presence of a catalyst to form a reaction product mixture, wherein said catalyst comprises a hydrotalcite; and
   (b) combining the reaction product mixture with an acid, wherein the acid is present in a molar ratio to the catalyst of from 1:1 to 10:1.

2. The process according to claim 1, wherein the acid comprises a mineral acid.

3. The process according to claim 2, wherein the mineral acid is selected from the group consisting of sulfuric acid, hydrochloric acid, phosphoric acid and mixtures thereof.

4. The process according to claim 1, wherein the acid comprises a carboxylic acid having from 1 to 4 carbon atoms.

5. The process according to claim 1, wherein the acid comprises a component selected from the group consisting of lactic acid, acetic acid, citric acid and mixtures thereof.

6. The process according to claim 1, wherein the catalyst further comprises a co-catalyst.

7. The process according to claim 1, wherein the acid is present in a molar ratio to the catalyst of from 1:1 to 4:1.

8. The process according to claim 1, wherein the reaction product mixture comprising an alkoxylated nonionic surfactant is combined with the acid at a temperature above the melting point of the alkoxylated nonionic surfactant.

9. The process according to claim 1, wherein the reaction product mixture is combined with the acid at a temperature of from about 70° C. to about 95° C.

10. The process according to claim 1, the acid comprises an aqueous solution.

11. The process according to claim 1, wherein the starting material comprises a methyl ester of a carboxylic acid having from 6 to 22 carbon atoms.

12. A process for preparing an alkoxylated nonionic surfactant, said process comprising:
    (a) reacting a carboxylic acid ester with an alkylene oxide in the presence of a catalyst to form a reaction product mixture, wherein said catalyst comprises a hydrotalcite; and
    (b) combining the reaction product mixture with an acid, said acid being present in at least an equimolar amount based on the amount of the catalyst present.

13. The process according to claim 12, wherein the acid comprises a mineral acid.

14. The process according to claim 13, wherein the mineral acid is selected from the group consisting of sulfuric acid, hydrochloric acid, phosphoric acid and mixtures thereof.

15. The process according to claim 12, wherein the acid comprises a carboxylic acid having from 1 to 4 carbon atoms.

16. The process according to claim 12, wherein the acid comprises a component selected from the group consisting of lactic acid, acetic acid, citric acid and mixtures thereof.

17. The process according to claim 12, wherein the catalyst further comprises a co-catalyst.

18. The process according to claim 12, wherein the acid is present in a molar ratio to the catalyst of from 1:1 to 4:1.

19. The process according to claim 12, wherein the reaction product mixture comprising an alkoxylated nonionic surfactant is combined with the acid at a temperature above the melting point of the alkoxylated nonionic surfactant.

20. The process according to claim 12, wherein the reaction product mixture is combined with the acid at a temperature of from about 70° C. to about 95° C.

21. The process according to claim 12, wherein the acid comprises an aqueous solution.

22. The process according to claim 12, wherein the starting material comprises a methyl ester of a carboxylic acid having from 6 to 22 carbon atoms.

23. A process for preparing an alkoxylated nonionic surfactant, said process comprising:
 (a) reacting a starting material selected from the group consisting of compounds having at least one active hydrogen atom, carboxylic acid esters and mixtures thereof with an alkylene oxide in the presence of a catalyst to form a reaction product mixture, wherein said catalyst comprises a hydrotalcite; and
 (b) combining the reaction product mixture with a mineral acid, said mineral acid being present in at least an equimolar amount based on the amount of the catalyst present.

24. The process according to claim 23, wherein the mineral acid is selected from the group consisting of sulfuric acid, hydrochloric acid, phosphoric acid and mixtures thereof.

25. The process according to claim 23, wherein the catalyst further comprises a co-catalyst.

26. The process according to claim 23, wherein the acid is present in a molar ratio to the catalyst of from 1:1 to 4:1.

27. The process according to claim 23, wherein the reaction product mixture comprising an alkoxylated nonionic surfactant is combined with the acid at a temperature above the melting point of the alkoxylated nonionic surfactant.

28. The process according to claim 23, wherein the reaction product mixture is combined with the acid at a temperature of from about 70° C. to about 95° C.

29. The process according to claim 23, wherein the acid comprises an aqueous solution.

30. The process according to claim 23, wherein the starting material comprises a methyl ester of a carboxylic acid having from 6 to 22 carbon atoms.

31. A process for preparing an alkoxylated nonionic surfactant, said process comprising:
 (a) reacting a starting material selected from the group consisting of compounds having at least one active hydrogen atom, carboxylic acid esters and mixtures thereof with an alkylene oxide in the presence of a catalyst system to form a reaction product mixture, wherein said catalyst system comprises a hydrotalcite and a co-catalyst; and
 (b) combining the reaction product mixture with an acid, said acid being present in at least an equimolar amount based on the amount of the catalyst present.

32. The process according to claim 31, wherein the acid comprises a mineral acid.

33. The process according to claim 32, wherein the mineral acid is selected from the group consisting of sulfuric acid, hydrochloric acid, phosphoric acid and mixtures thereof.

34. The process according to claim 31, wherein the acid comprises a carboxylic acid having from 1 to 4 carbon atoms.

35. The process according to claim 31, wherein the acid comprises a component selected from the group consisting of lactic acid, acetic acid, citric acid and mixtures thereof.

36. The process according to claim 31, wherein the acid is present in a molar ratio to the catalyst of from 1:1 to 4:1.

37. The process according to claim 31, wherein the reaction product mixture comprising an alkoxylated nonionic surfactant is combined with the acid at a temperature above the melting point of the alkoxylated nonionic surfactant.

38. The process according to claim 31, wherein the reaction product mixture is combined with the acid at a temperature of from about 70° C. to about 95° C.

39. The process according to claim 31, wherein the acid comprises an aqueous solution.

40. The process according to claim 31, wherein the staring material comprises a methyl ester of a carboxylic acid having from 6 to 22 carbon atoms.

41. A method of treating a hydrotalcite catalyst-containing composition, said method comprising:
 (a) providing a mixture comprising an alkoxylated nonionic surfactant and a hydrotalcite catalyst; and
 (b) combining the mixture and an acid, wherein the acid is present in a molar ratio to the catalyst of from 1:1 to 10:1.

42. The method according to claim 41, wherein the mixture further comprises a co-catalyst.

43. The method according to claim 41, wherein the acid is present in a molar ratio to the catalyst of from 1:1 to 4:1.

44. The method according to claim 42, wherein the acid is present in a molar ratio to the combined catalyst and co-catalyst of from 1:1 to 4:1.

45. A process for preparing an alkoxylated nonionic surfactant, said process comprising:
 (a) reacting a starting material containing a methyl ester of a carboxylic acid having from 6 to 22 carbon atoms with an alkylene oxide in the presence of a catalyst to form a reaction product mixture containing an alkoxylated nonionic surfactant, wherein said catalyst comprises a hydrotalcite; and
 (b) combining the reaction product mixture with an acid selected from the group consisting of lactic acid, acetic acid, citric acid and mixtures thereof, at a temperature above the melting point of the alkoxylated nonionic surfactant; said acid being present in a molar ratio to the catalyst of from 1:1 to 4:1.

* * * * *